US012797006B2

(12) United States Patent
Baudu et al.

(10) Patent No.: US 12,797,006 B2
(45) Date of Patent: Nov. 17, 2026

(54) METHOD FOR DETECTING AN INAPPROPRIATE POSTURE OF AN OCCUPANT SEATED ON A VEHICLE SEAT

(71) Applicant: FAURECIA Sièges d'Automobile, Nanterre (FR)

(72) Inventors: Samuel Baudu, Boulogne (FR); Nour Besbes, Montrouge (FR); Hichem Mouldi, Chaville (FR)

(73) Assignee: FAURECIA Sièges d'Automobile, Nanterre (FR)

( * ) Notice: Subject to any disclaimer, the term of this patent is extended or adjusted under 35 U.S.C. 154(b) by 14 days.

(21) Appl. No.: 19/009,356

(22) Filed: Jan. 3, 2025

(65) Prior Publication Data

US 2025/0221660 A1 Jul. 10, 2025

(30) Foreign Application Priority Data

Jan. 5, 2024 (FR) ...................................... 2400114

(51) Int. Cl.
*A61B 5/00* (2006.01)
*G08B 21/04* (2006.01)

(52) U.S. Cl.
CPC ........ *A61B 5/4561* (2013.01); *G08B 21/0461* (2013.01)

(58) Field of Classification Search
CPC .............. A61B 5/4561; G08B 21/0461; B60N 2210/40; B60N 2/0027; B60N 2/003; B60N 2/002; B60N 2210/12; B60N 2/0021; B60N 2/0028; B60Q 9/00; B60R 21/01532; G01L 1/142
See application file for complete search history.

(56) References Cited

U.S. PATENT DOCUMENTS 11,254,238 B2 * 2/2022 Lin ...................... B60N 2/0021
11,383,662 B2 * 7/2022 Schaub ................ B60N 2/0025
11,807,136 B2 11/2023 Balde
2022/0266724 A1 * 8/2022 Baudu ...................... B60Q 9/00

FOREIGN PATENT DOCUMENTS

FR 3126776 A1 3/2023

OTHER PUBLICATIONS

French Search Report for French App. No. FR2400114 dated Jul. 30, 2024, 8 pages, No English Translation Available.

* cited by examiner

*Primary Examiner* — Brian Wilson
(74) *Attorney, Agent, or Firm* — Barnes & Thornburg LLP

(57) ABSTRACT

The present disclosure relates to a method for detecting an inappropriate posture of an occupant seated on a seat of a vehicle, the method comprising the following steps:
after a first defined duration following detection of the presence of an occupant on the seat,
for each pressure sensor of the detection system:
a) determining a characteristic value representative of the capacitive values measured by the pressure sensor considered over a first period,
b) determining a permissible variation range defined for the sensor considered based on the characteristic value,
c) determining the absence of pressure on a zone on the basis of the permissible variation range defined for the sensor considered and the capacitive values measured over a subsequent period,
generating a warning signal when an absence of pressure has been determined on at least one zone.

10 Claims, 6 Drawing Sheets

METHOD FOR DETECTING AN INAPPROPRIATE POSTURE OF AN OCCUPANT SEATED ON A VEHICLE SEAT

PRIORITY CLAIM

This application claims priority to French Patent Application FR2400114, field Jan. 5, 2024, which is expressly incorporated by reference herein.

BACKGROUND

The present disclosure relates to a method for detecting an inappropriate posture of an occupant seated on a seat of vehicle, especially a motor vehicle.

SUMMARY

According to the present disclosure, a method for detecting an inappropriate posture of an occupant seated on a seat of a vehicle, especially a motor vehicle is provided. The seat having a seat base and a backrest articulated at the seat base, the backrest comprising two lateral edges, an upper edge and a lower edge adjacent to the seat base; a first vertical central plane extending between and midway between the two lateral edges, a first horizontal central plane extending between and midway between the upper edge and the lower edge; the method being implemented by a detection system comprising a processor, at least a first pressure sensor arranged on a first zone located on one side of the first vertical central plane and above the first horizontal central plane, a second pressure sensor arranged on a second zone located on the other side of the first vertical central plane and above the first horizontal central plane, a third pressure sensor arranged on a third zone located on the side of the first vertical central plane and below the first horizontal central plane, a fourth pressure sensor arranged on a fourth zone located on the other side of the first vertical central plane and below the first horizontal central plane; the method comprising a step of activating a measurement phase comprising time periods during which capacitive values are measured by the first, second, third and fourth pressure sensors; the method further comprising the following steps implemented by the processor during the measurement phase:

upon detection of the presence of an occupant on the seat, activating a clock suitable for signaling the end of a first defined duration;

after the first defined duration, considering each pressure sensor from the first, second, third and fourth pressure sensors, for each pressure sensor considered:

a) determining a characteristic value representative of the capacitive values measured by the pressure sensor considered over a first period, b) determining a permissible variation range defined for the sensor considered based on the characteristic value, c) determining the presence or absence of pressure on a zone on the basis of the permissible variation range defined for the sensor considered and the capacitive values measured over a subsequent period by the pressure sensor considered arranged in the zone, generating a warning signal when an absence of pressure has been determined on at least one zone from the zones considered.

The features disclosed in the following paragraphs may optionally be implemented. They can be implemented independently of one another or in combination with one another:

the step of determining the presence or absence of pressure on a zone comprises the following steps:

i) determining a subsequent characteristic value representative of the capacitive values measured by the pressure sensor considered over a subsequent period, ii) comparing the subsequent characteristic value with the permissible variation range defined for the sensor considered;

iii) determining an absence of pressure on the zone considered if the subsequent characteristic value does not lie within the permissible variation range defined for the sensor considered, or determining the presence of pressure if the subsequent characteristic value does lie within the permissible variation range defined for the sensor considered.

The method further comprises a step of repeating steps i) to iii) for a second defined duration and wherein the step of generating a warning signal is implemented only if an absence of pressure is determined continuously for a duration at least equal to the second defined duration.

If a presence of pressure has been determined on the first zone and on the second zone and the absence of pressure has been determined on the third zone and on the fourth zone, then the warning signal generated is representative of a forward pelvis position of the occupant of the seat.

If an absence of pressure has been determined on the first and third zones, and a presence of pressure has been determined on the second zone and the fourth zone, then the warning signal generated is representative of a position of the torso turned to the side.

If an absence of pressure has been determined on the first zone and on the second zone and a presence of pressure has been determined on the third zone and on the fourth zone, then the warning signal generated is representative of a forward-leaning position of the occupant of the seat.

the seat base 4 comprises a front edge and a rear edge, a vertical transverse plane being defined midway between the front edge of the seat base and the rear edge of the seat base, the detection device comprises at least a first front pressure sensor arranged on a front zone of the seat base located in front of the vertical transverse plane, and a first rear pressure sensor arranged on a rear zone of the seat base located behind the vertical transverse plane; the method comprising the following steps:

considering each pressure sensor from the first front pressure sensor and the rear pressure sensor, for each sensor considered:

a) determining a characteristic value representative of the capacitive values measured by the pressure sensor considered over a first period, b) determining a permissible variation range defined for the sensor considered based on the characteristic value, c) determining the presence or absence of pressure on a zone on the basis of the permissible variation range defined for the sensor considered and the capacitive values measured over a subsequent period by the pressure sensor considered arranged in the zone, generating a warning signal when an absence of pressure has been determined on the rear zone, the warning signal generated being representative of a forward pelvis position of the occupant of the seat.

The seat comprises two lateral edges, a second vertical central plane being defined midway between the two lateral edges of the seat base, the front zone comprises a first front zone of the seat base arranged on one side of the second vertical central plane, and a second front zone of the seat base arranged on the other side of the second vertical central plane, the rear zone comprises a first rear zone of the seat base located on one side of the second vertical central plane, and a second rear zone of the seat base located on the other side of the second vertical central plane, the detection device comprises a second front pressure sensor arranged on the second front zone, the first front pressure sensor being located on the first front zone, the detection device further comprises a second rear pressure sensor arranged on the second rear zone, the first rear pressure sensor being located on the first rear zone, the method comprising the following steps:

considering each pressure sensor from the second front pressure sensor and the second rear pressure sensor for each sensor considered:

a) determining a characteristic value representative of the capacitive values measured by the pressure sensor considered over a first period, b) determining a permissible variation range defined for the sensor considered based on the characteristic value, c) determining the presence or absence of pressure on a zone on the basis of the permissible variation range defined for the sensor considered and the capacitive values measured over a subsequent period by the pressure sensor considered arranged in the zone, generating a warning signal when an absence of pressure has been determined on the first front zone or on the second front zone, the warning signal generated being representative of a position of a leg crossed over the other leg of the occupant of the seat.

The present disclosure also relates to at A): a method for detecting an inappropriate posture of an occupant seated on a seat of a vehicle, especially a motor vehicle; the seat having a seat base and a backrest articulated at the seat base, the backrest comprising two lateral edges, a first vertical central plane extending between and midway between the two lateral edges; the method being implemented by a detection system comprising a processor, at least a first pressure sensor arranged on a first zone located on one side of the first vertical central plane, and a second pressure sensor arranged on a second zone located on the other side of the first vertical central plane; the method comprising a step of activating a measurement phase comprising time periods during which capacitive values are measured by the first and the second pressure sensors; the method further comprising the following steps implemented by the processor during the measurement phase:

upon detection of the presence of an occupant on the seat, activating a clock suitable for signaling the end of a first defined duration;

after the first defined duration, considering each pressure sensor from the first pressure sensor and the second pressure sensor, for each sensor considered:

a) determining a characteristic value representative of the capacitive values measured by the pressure sensor considered over a first period, b) determining a permissible variation range defined for the sensor considered based on the characteristic value, c) determining the presence or absence of pressure on a zone on the basis of the permissible variation range defined for the sensor considered and the capacitive values measured during a subsequent period by the pressure sensor considered arranged in the zone, generating a warning signal when an absence of pressure has been determined on at least one zone from the first zone and the second zone (Z2).

The present disclosure also relates to at B): a method for detecting an inappropriate posture of an occupant seated on a seat of a vehicle, especially a motor vehicle; the seat having a seat base and a backrest articulated at the seat base, the backrest comprising an upper edge and a lower edge adjacent to the seat base; a horizontal central plane extending midway between the upper edge and the lower edge; the method being implemented by a detection system comprising a processor, at least a first pressure sensor arranged on a first zone located above the horizontal central plane, and a second pressure sensor arranged on a second zone located below the horizontal central plane; the method comprising a step of activating a measurement phase comprising time periods during which capacitive values are measured by the first and the second pressure sensors; the method further comprising the following steps implemented by the processor during the measurement phase:

upon detection of the presence of an occupant on the seat, activating a clock suitable for signaling the end of a first defined duration;

after the first defined duration, considering each pressure sensor from the first pressure sensor and the second pressure sensor, for each sensor considered:

a) determining a characteristic value representative of the capacitive values measured by the pressure sensor considered over a first period, b) determining a permissible variation range defined for the sensor considered based on the characteristic value, c) determining the presence or absence of pressure on a zone on the basis of the permissible variation range defined for the sensor considered and the capacitive values measured during a subsequent period by the pressure sensor considered arranged in the zone, generating a warning signal when an absence of pressure has been determined on at least one zone from the first zone and the second zone.

According to one embodiment, in the detection method according to (A) and (B), the step of determining the presence or absence of pressure on a zone comprises the following steps:

i) determining a subsequent characteristic value representative of the capacitive values measured by the pressure sensor considered over a subsequent period, ii) comparing the subsequent characteristic value with the permissible variation range defined for the sensor considered;

iii) determining that there is no pressure on the zone considered if the subsequent characteristic value does not lie within the permissible variation range defined for the sensor considered, or determining a presence of pressure when the subsequent characteristic value does lie within the permissible variation range defined for the sensor considered.

According to one embodiment, the detection method according to A) and B) further comprises a step of repeating steps i) to iii) for a second defined duration and wherein the step of generating a warning signal is implemented only if an absence or presence of pressure is determined continuously for a duration greater than the second defined duration.

In the detection method according to A), if an absence of pressure has been determined in the first zone and a presence of pressure has been determined in the second zone, then the warning signal generated is representative of a position of the torso turned to the side.

According to one embodiment, in the detection method according to B), if an absence of pressure has been determined in the first zone and in the second zone, then the warning signal generated is representative of a forward-leaning position of the occupant of the seat.

According to one embodiment, in the detection method according to A) and B), the seat base comprises a front edge and a rear edge, a vertical transverse plane being defined between and midway between the front edge of the seat base and the rear edge of the seat base, the detection device comprises at least a first front pressure sensor arranged on a front zone of the seat base located in front of the vertical transverse plane, and a first rear pressure sensor arranged on a rear zone of the seat base located behind the vertical transverse plane, the method comprising the following steps:

considering each pressure sensor from the first front pressure sensor and the first rear pressure sensor, for each sensor considered:

a) determining a characteristic value representative of the capacitive values measured by the pressure sensor considered over a first period, b) determining a permissible variation range defined for the sensor considered based on the characteristic value, c) determining the presence or absence of pressure on a zone on the basis of the permissible variation range defined for the sensor considered and the capacitive values measured during a subsequent period by the pressure sensor considered arranged in the zone, generating a warning signal when an absence of pressure has been determined on the rear zone, the warning signal generated being representative of a forward pelvis position of the occupant of the seat.

According to one embodiment, in the detection method according to A) and B), the seat base comprises two lateral edges, a second vertical central plane being defined midway between the two lateral edges of the seat base, the front zone comprises a first front zone of the seat base arranged on one side of the second vertical central plane and a second front zone of the seat base arranged on the other side of the second vertical central plane, the rear zone comprises a first rear zone of the seat base located on one side of the second vertical central plane, and a second rear zone of the seat base located on the other side of the second vertical central plane, the detection device comprises a second front pressure sensor arranged on the second front zone, the first front pressure sensor being located on the first front zone, the detection device further comprises a second rear pressure sensor arranged on the second rear zone, the first rear pressure sensor being located on the first rear zone, the method comprising the following steps:

considering each pressure sensor from the second front pressure sensor and the second rear pressure sensor, for each sensor considered:

a) determining a characteristic value representative of the capacitive values measured by the pressure sensor considered over a first period, b) determining a permissible variation range defined for the sensor considered based on the characteristic value, c) determining the presence or absence of pressure on a zone on the basis of the permissible variation range defined for the sensor considered and the capacitive values measured over a subsequent period by the pressure sensor considered arranged in the zone, generating a warning signal when an absence of pressure has been determined on the first front zone or on the second front zone, the warning signal generated being representative of a position of a leg crossed over the other leg of the occupant of the seat.

Additional features of the present disclosure will become apparent to those skilled in the art upon consideration of illustrative embodiments exemplifying the best mode of carrying out the disclosure as presently perceived.

BRIEF DESCRIPTIONS OF THE DRAWINGS

The detailed description particularly refers to the accompanying figures in which.

DETAILED DESCRIPTION

In this patent application, identical or similar elements bear the same references and will not be described a second time.

In the present application, the terms “upper”, “lower”, “in front of”, “behind”, “front”, “rear” are to be interpreted with respect to the usual position of a seat of a motor vehicle. The front of the seat of a vehicle corresponds to the front of the vehicle considering the normal direction of travel of the vehicle.

In the present application, the longitudinal direction X means a horizontal direction extending between the front and the rear of the vehicle seat. The transverse direction Y means a horizontal direction, extending from one side of the seat to the other side of the seat. The vertical direction Z means the direction perpendicular to the longitudinal X and transverse Y directions.

A motor vehicle seat 2 comprises a seat base 4, a backrest 6 which is articulated at the seat base 4.

Figure 1:
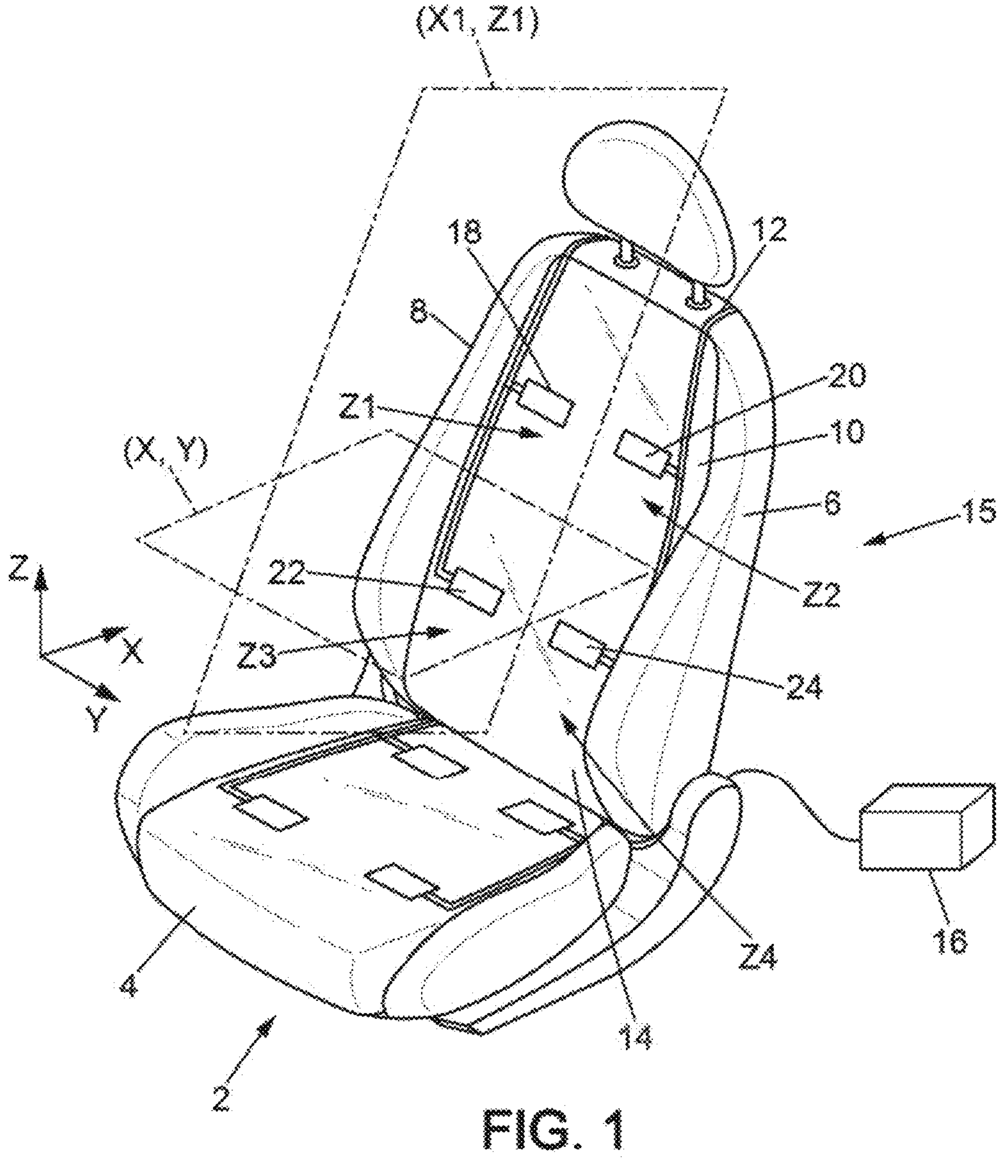
FIG. 1 is a schematic perspective view of a seat and a detection system according to a first embodiment of the present disclosure.

Referring to FIG. 1, the backrest 6 comprises two lateral edges 8, 10, an upper edge 12 and a lower edge 14 adjacent to the seat base.

For the purposes of this patent application, a first vertical central plane (X1, Z1) is defined, extending between and midway between the two lateral edges 8, 10, and a first horizontal central plane (X, Y) is defined, extending between and midway between the upper edge 12 and the lower edge 14 of the backrest.

The planes define four zones on the backrest.

In particular, a first zone Z1 is located on one side of the first vertical central plane (X1, Z1) and above the first horizontal central plane (X, Y). A second zone Z2 is located on the other side of the first vertical central plane (X1, Z1) and above the first horizontal central plane (X, Y).

A third zone Z3 is located on the side of the first vertical central plane (X1, Z1) and below the first horizontal central plane (X, Y). A fourth zone Z4 is located on the other side of the first vertical central plane (X1, Z1) and below the first horizontal central plane (X, Y).

The detection method according to a first embodiment is implemented by a detection system 15 according to a first embodiment comprising a processor 16, and at least four pressure sensors arranged on the backrest.

Referring to FIG. 1, the sensors located on the backrest comprise a first pressure sensor 18 arranged on the first zone Z1, a second pressure sensor 20 arranged on the second zone Z2, a third pressure sensor 22 arranged on a third zone Z3, a fourth pressure sensor 24 arranged on the fourth zone Z4 of the backrest.

According to an advantageous and non-limiting variant, the detection method according to the first embodiment is implemented by a detection system 15 further comprising four pressure sensors on the seat base.

Figure 2:
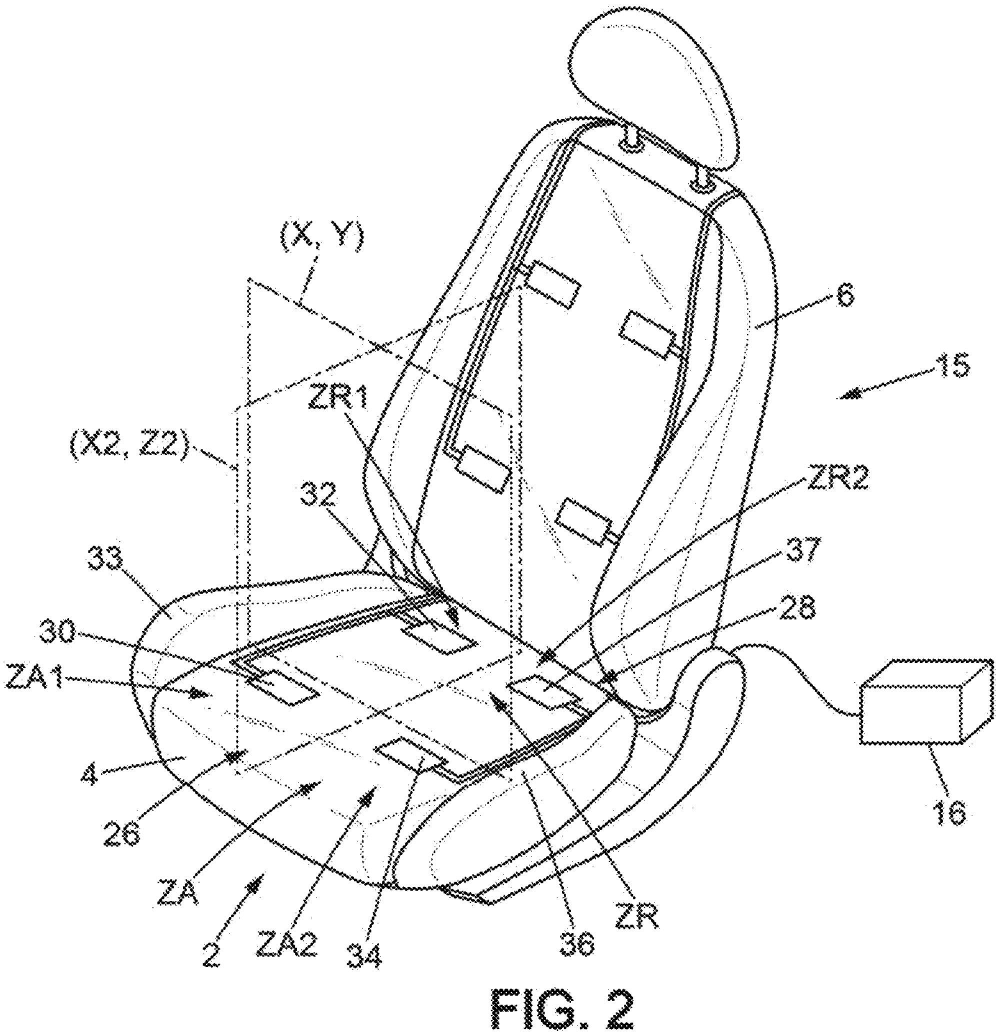
FIG. 2 is a schematic perspective view of the seat and a part of a detection system that can be added to the detection system shown in FIG. 1.

In particular, referring to FIG. 2, the seat base 4 comprises a front edge 26, a rear edge 28 and two lateral edges 33, 36.

For the purposes of the present patent application, a vertical transverse plane (Y, Z) is defined, located midway between the front edge 26 of the seat base and the rear edge 28 of the seat base, and a second vertical central plane (X2, Z2) is defined, located midway between the two lateral edges 33, 36 of the seat base.

The seat base 4 comprises a front zone ZA located in front of the vertical transverse plane (Y, Z), and a rear zone ZR located behind the vertical transverse plane (Y, Z). In particular, the seat base comprises a first front zone ZA1 of the seat base arranged on one side of the second vertical central plane (Y, Z), and a second front zone ZA2 of the seat base arranged on the other side of the second vertical central plane (Y, Z). Similarly, the rear zone ZR of the seat base 4 comprises a first rear zone ZR1 located on one side of the second vertical central plane (Y, Z), and a second rear zone ZR2 located on the other side of the second vertical central plane (Y, Z).

Referring to FIG. 2, the sensors located on the seat base comprise a first front pressure sensor 30 arranged on the first front zone ZA1 of the seat base, a second front pressure sensor 34 arranged on the second front zone ZA2, a first rear pressure sensor 32 located on the first rear zone ZR1, and a second rear pressure sensor 37 arranged on the second rear zone ZR2.

The pressure sensors are, for example, capacitive sensors with coplanar interdigitated electrodes as described in the patent application published under number FR3126776 and is incorporated by reference herein in its entirety.

Figure 3:
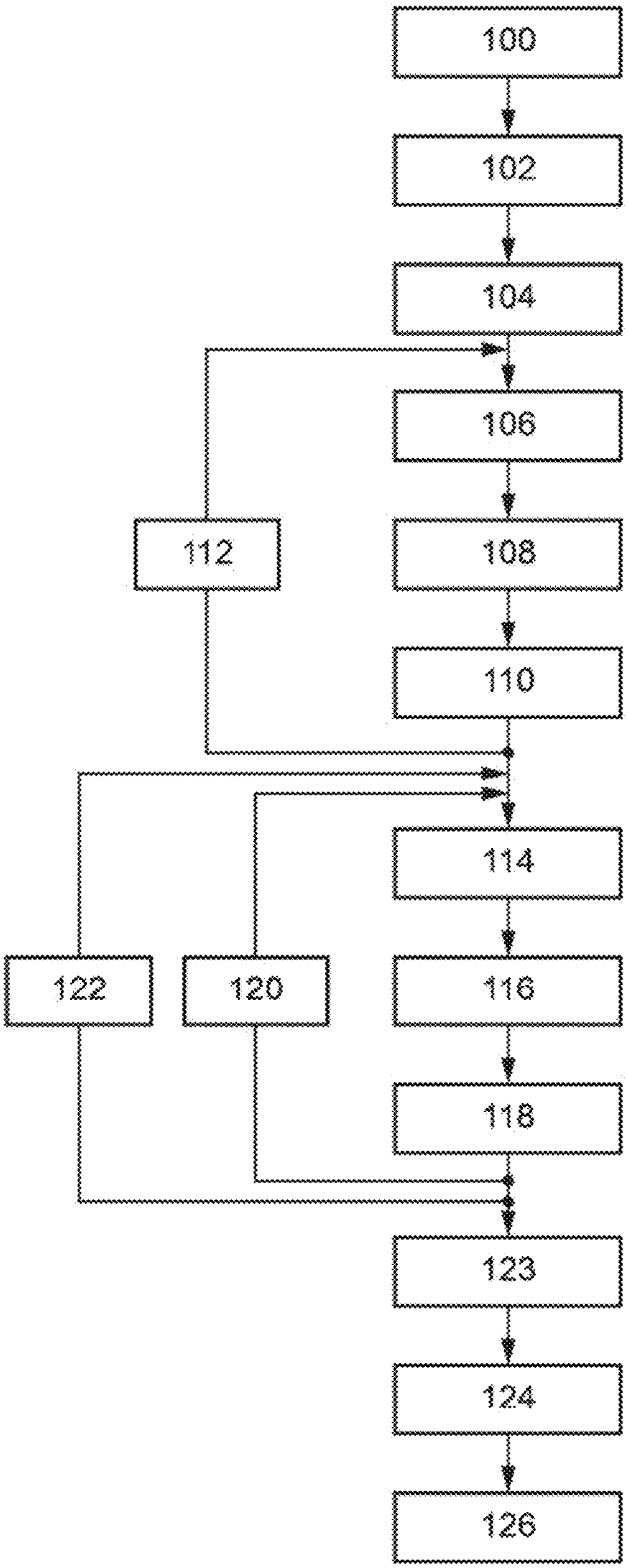
FIG. 3 is a diagram showing the steps of the detection method according to the present disclosure.

Referring to FIG. 3, the method for detecting an inappropriate posture begins with a step 100 of activating a measurement phase. During the measurement phase, capacitive values generated by the pressure sensors 18 to 24 are measured at regular time intervals. The measurement phase comprises periods of time during which several measurements are taken. The measurement phase is implemented continuously during all steps of the method. Steps 114 to 124 are repeated with the new capacitative values measured during the measurement phase.

The method then comprises a step 102 of detecting the presence of an occupant on the seat. This step can be carried out using capacitative values measured according to a suitable procedure or by other means such as a camera and image recognition system. Once the presence of an occupant has been detected on the seat, a clock is started in step 104. The clock is configured to signal the end of a first defined duration D1.

Then, after the first defined duration, each pressure sensor from the first, second, third and fourth pressure sensors is considered.

Steps 106 to 122 are carried out for each pressure sensor considered.

In step 106, a characteristic value representative of the capacitive values generated by each pressure sensor considered is determined. This characteristic value is representative of the capacitive values measured over a first period. The first period is the first period following the first defined duration D1. This characteristic value is, for example, an average value of the capacitive values measured during the first period. Alternatively, the characteristic value is a median value of the capacitive values measured during the first period.

In step 108, a permissible variation range defined for the sensor considered is determined. This permissible variation range is determined based on the characteristic value. For example, the lower value of the permissible variation range is equal to the characteristic value minus 15% of the characteristic value and the upper value of the permissible variation range is equal to the characteristic value plus 15% of the characteristic value.

According to another example, the lower value of the permissible variation range is equal to the characteristic value minus 20% of the characteristic value and the upper value of the permissible variation range is equal to the characteristic value plus 20% of the characteristic value.

In step 110, the permissible variation range defined in step 108 is stored in the memory of the processor 16.

In step 112, the method returns to step 106, another pressure sensor is considered, and steps 106 to 110 are implemented for this other sensor. Steps 106 to 110 are thus implemented for each pressure sensor.

During steps 114 to 122, each zone is considered and the presence or absence of pressure is determined on each zone considered from the capacitive values measured by the pressure sensors arranged in the zones considered. The zones considered are the first zone Z1, the second zone Z2, the third zone and the fourth zone Z4 of the backrest, as well as the first front zone ZA1, the second front zone ZA2, the first rear zone ZR1 and the second rear zone ZR2 of the seat base.

In step 114, a next characteristic value is determined from the capacitive values generated over a subsequent period by the pressure sensor considered. This subsequent characteristic value is representative of the capacitive values measured over a subsequent period. In the present patent application, “subsequent period” means the period immediately following the first period, as well as all subsequent periods. Step 114 will be repeated for each new period throughout the duration of the measurement phase. This subsequent characteristic value is, for example, an average value of the capacitive values measured during a subsequent period. Alternatively, the subsequent characteristic value is a median value of the capacitive values measured during a subsequent period.

In step 116, the subsequent characteristic value is compared with the permissible variation range defined for the sensor considered and stored in the memory of the processor.

When the subsequent characteristic value is within the permissible variation range, a presence of pressure in the zone considered is determined in step 118. If the subsequent characteristic value is outside the permissible variation range, an absence of pressure in the zone considered is determined in step 118.

Steps 114 to 118 are repeated for all pressure sensors in step 120.

Preferably, the method comprises step 122 during which steps 114 to 118 are repeated on the basis of the capacitive values generated by the pressure sensors over subsequent periods. These steps 114 to 118 are repeated several times over a duration at least equal to the second defined duration D2. And steps 123 and 124 are only implemented if no pressure has been detected during the second defined duration.

Then, in step 123, the set of statuses of pressure presence and of pressure absence is analyzed in order to determine whether the occupant of the seat has an inappropriate position on the seat.

In step 124, a warning signal is generated when an absence of pressure has been determined on at least one zone from the zones considered.

In particular, if a presence of pressure has been determined in the first zone Z1 and in the second zone Z2 and an absence of pressure has been determined in the third zone Z3 and in the fourth zone Z4, then the warning signal generated is representative of a forward pelvis position of the occupant of the seat.

When the seat comprises four sensors on the seat base in addition to the four sensors on the backrest, the warning signal representative of a forward pelvis position of the occupant of the seat is confirmed by determining an absence of pressure on the first rear zone ZR1 from the capacitive values measured by the first rear pressure sensor 32 and on the second rear zone ZR2 from the capacitive values measured by the second rear pressure sensor 37.

When an absence of pressure has been determined on the first zone Z1 and on the third zone Z3, and a presence of pressure has been determined on the second zone Z2 and on the fourth zone Z4, then the warning signal generated is representative of a position of the torso turned to the side.

When an absence of pressure has been determined on the second zone Z2 and on the fourth zone Z4, and a presence of pressure has been determined on the first zone Z1 and on the third zone Z3, then the warning signal generated is also representative of a position of the torso turned to the side.

When an absence of pressure has been determined on the first zone Z1 and on the second zone Z2 and a presence of pressure has been determined on the third zone Z3 and in the fourth zone Z4, then the warning signal generated is representative of a forward-leaning position of the occupant of the seat.

When an absence of pressure has been determined on the first front zone ZA1 or on the second front zone ZA2, the warning signal generated is representative of a position of a leg crossed over the other leg of the occupant of the seat.

In step 126, the warning signal may be transmitted to a display device to display an image corresponding to the type of inappropriate posture detected. Alternatively, the warning signal is transmitted to a sound system emitting an audible alert or to a voice system able to select a voice message corresponding to the type of inappropriate posture detected.

Figure 4:
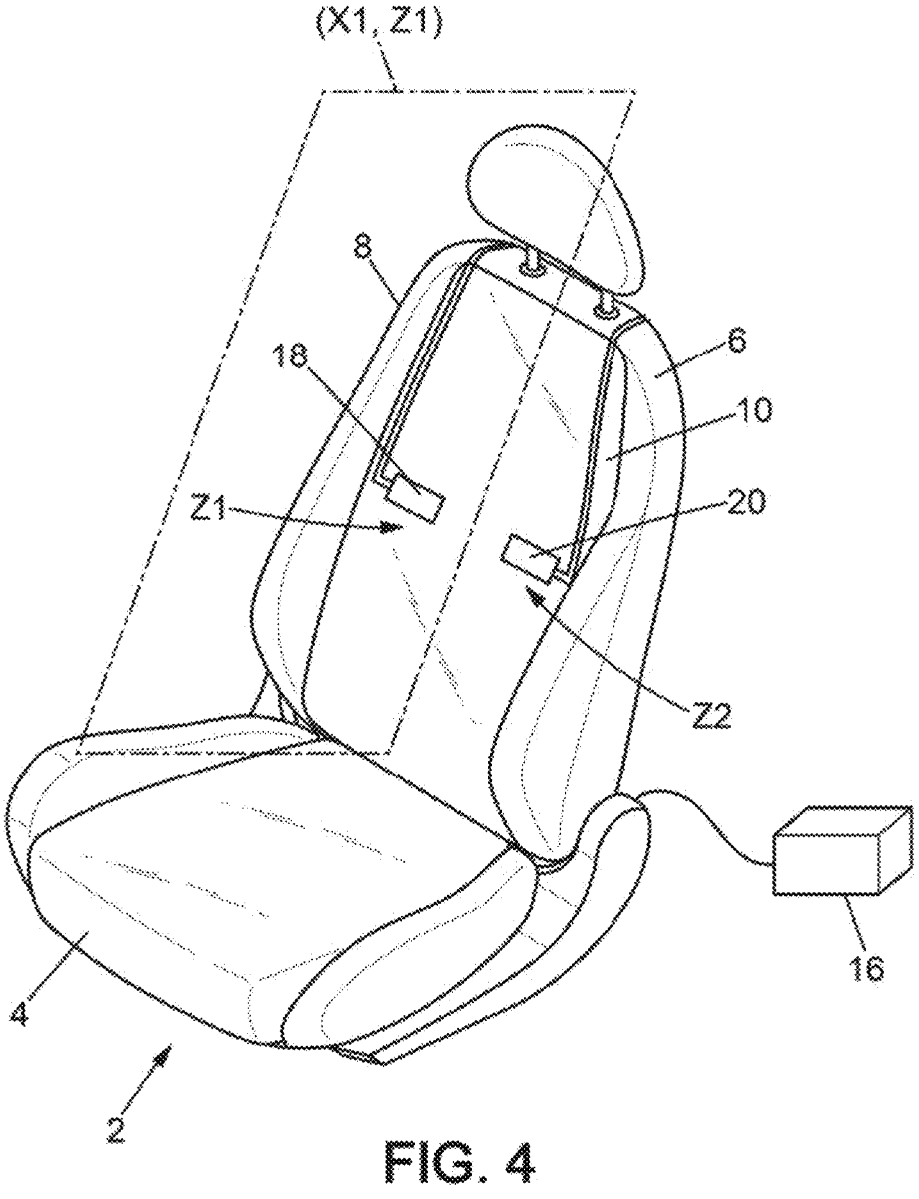
FIG. 4 is a schematic perspective view of a seat and a detection system according to a second embodiment.

FIG. 4 shows a detection system according to a second embodiment which can implement the detection method according to the present disclosure. In this second embodiment, the detection system 15 comprises a processor 16, at least a first pressure sensor 18 arranged on a first zone Z1 located on a side of the first vertical central plane (X1, Z1), and a second pressure sensor 20 arranged on a second zone Z2 located on the other side of the first vertical central plane (X1, Z1). The first vertical central plane (X1, Z1) being defined as the first vertical central plane (X1, Z1) shown in FIG. 1.

Steps 100 to 124 of the detection method according to the present disclosure can be implemented by the detection system according to the second embodiment.

In particular, the detection system according to the second embodiment comprises a step for determining the presence or absence of pressure on a zone. This step comprises the following steps:

i) determining 114 a subsequent characteristic value representative of the capacitive values measured by the pressure sensor considered over a subsequent period, ii) comparing 116 the subsequent characteristic value with the permissible variation range defined for the sensor considered;

iii) determining 118 an absence of pressure on the zone considered if the subsequent characteristic value does not lie within the permissible variation range defined for the sensor considered or determining a presence of pressure if the subsequent characteristic value does lie within the permissible variation range defined for the sensor considered.

The method for detecting an inappropriate posture implemented by the second detection system further comprises a step 122 of repeating steps i) to iii) for a second defined duration D2. The step of generating a warning signal is implemented only if an absence or a presence of pressure is determined continuously for a duration greater than the second defined duration.

In this embodiment, when an absence of pressure has been determined in the first zone Z1 and a presence of pressure has been determined in the second zone Z2, then the warning signal generated is representative of a position of the torso turned to the side.

Figure 6:
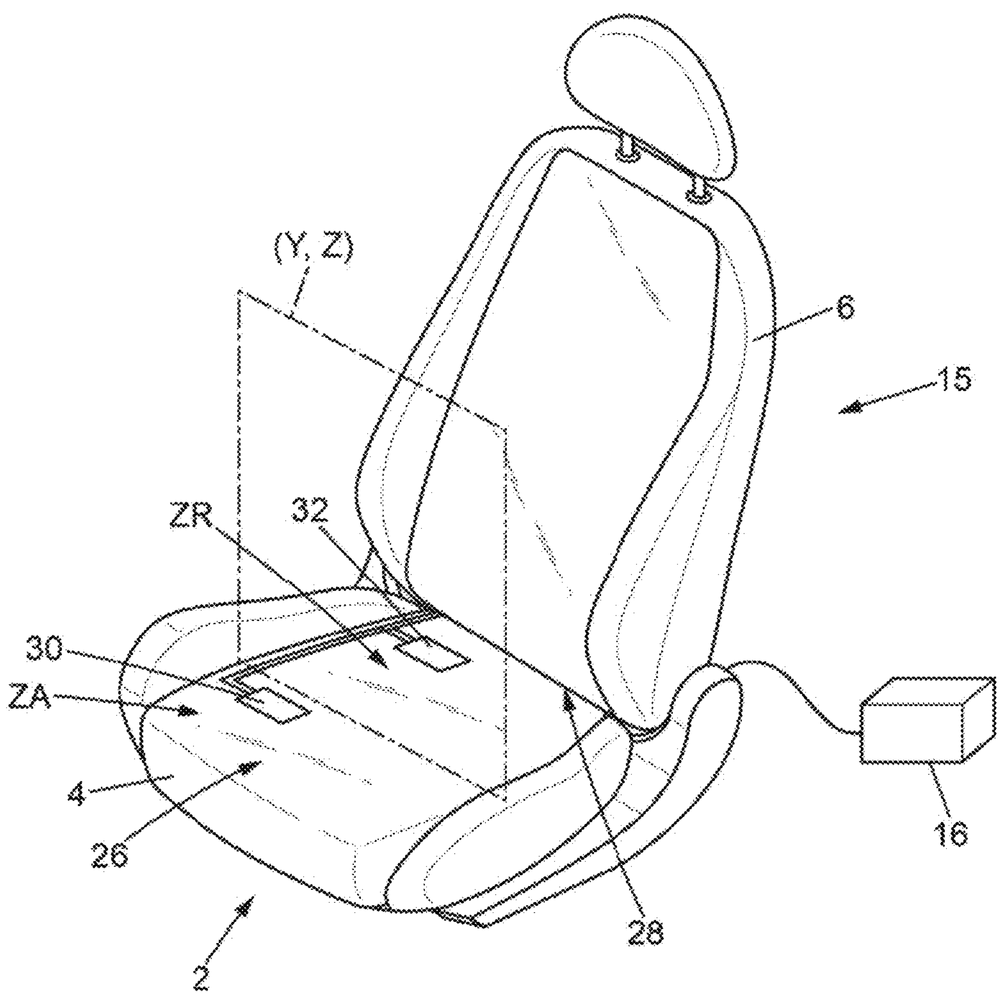
FIG. 6 is a schematic perspective view of a seat and a detection system according to a fourth embodiment.

Preferably, the detection device 15 according to the second embodiment further comprises a first front pressure sensor 30 and a first rear pressure sensor 32, as shown in FIG. 6. The first front pressure sensor 30 is arranged on a front zone ZA of the seat base in front of a vertical transverse plane (Y, Z). The first rear pressure sensor 32 is arranged on a rear zone ZR of the seat base behind the vertical transverse plane (Y, Z). The vertical transverse plane (Y, Z) is defined and positioned in the same way as the vertical transverse plane (Y, Z) shown in FIG. 1.

When an absence of pressure has been determined on the rear zone ZR, the warning signal generated is representative of a forward pelvis position of the occupant of the seat.

Alternatively, the detection device 15 according to the second embodiment further comprises four pressure sensors arranged on the seat base as shown in FIG. 1.

In this case, the seat base 4 comprises two lateral edges 33, 36. A second vertical central plane (X2, Z2) is defined midway between the two lateral edges of the seat base. The front zone ZA comprises a first front zone ZA1 of the seat base arranged on one side of the second vertical central plane and a second front zone ZA2 of the seat base arranged on the other side of the second vertical central plane (X2, Z2), the rear zone comprises a first rear zone ZR1 of the seat base located on one side of the second vertical central plane (X2, Z2), a second rear zone ZR2 of the seat base located on the other side of the second vertical central plane (X2, Z2).

The detection device 15 comprises a second front pressure sensor 34 arranged on the second front zone ZA2), while the first front pressure sensor 30 is located on the first front zone ZA1.

The detection device 15 further comprises a second rear pressure sensor 37 arranged on the second rear zone ZR2, while the first rear pressure sensor 32 is located on the first rear zone ZR1.

The detection method implemented by the second detection system comprises the following steps:

considering each pressure sensor from the second front pressure sensor 34 and the second rear pressure sensor 37, for each sensor considered:

a) determining 106 a characteristic value representative of the capacitive values measured by the pressure sensor considered over a first period, b) determining 108 a permissible variation range defined for the sensor considered based on the characteristic value, c) determining 114, 116, 118, 120 the presence or absence of pressure on a zone on the basis of the permissible variation range defined for the sensor considered and the capacitive values measured over a subsequent period by the pressure sensor considered arranged in the zone, and generating 124 a warning signal when an absence of pressure has been determined on the first front zone ZA1 or on the second front zone ZA2, the warning signal generated being representative of a position of a leg crossed over the other leg of the occupant of the seat.

Figure 5:
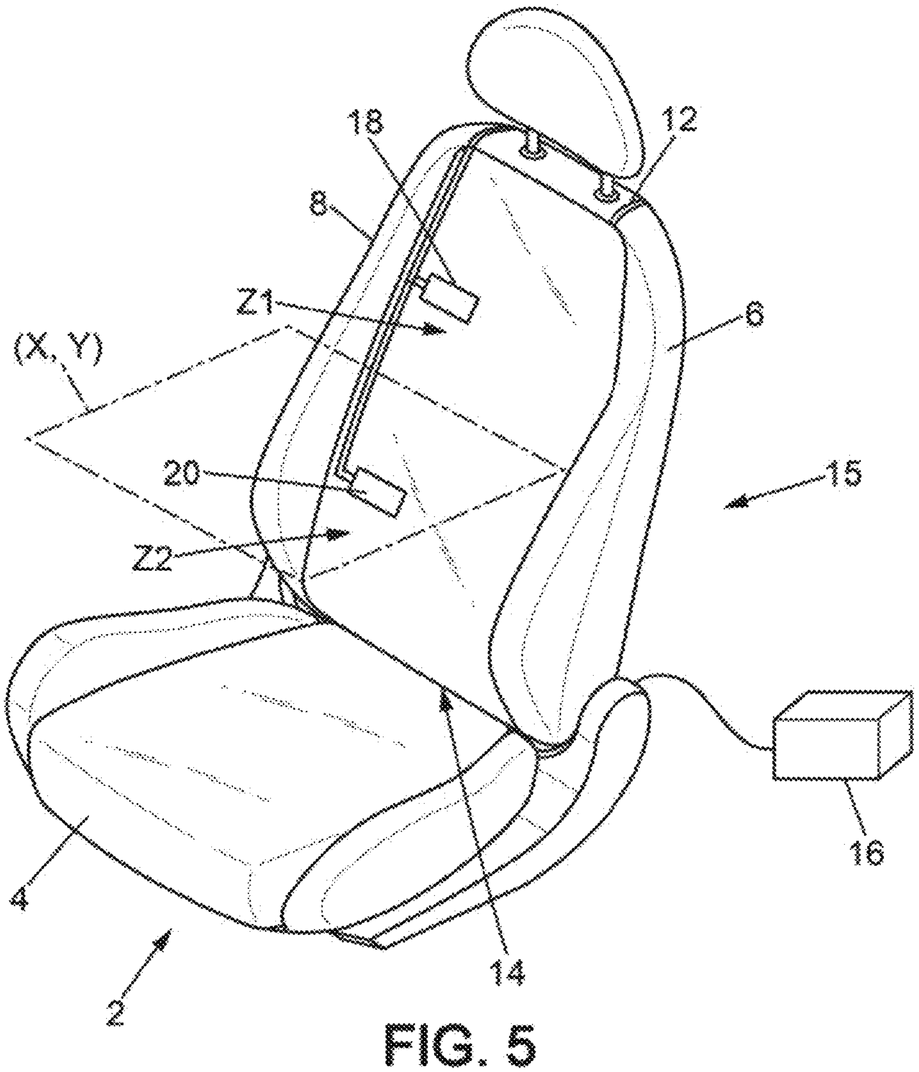
FIG. 5 is a schematic perspective view of a seat and a detection system according to a third embodiment.

FIG. 5 shows a detection system according to a third embodiment which can implement the detection method according to the present disclosure. In this third embodiment, a horizontal central plane (X, Y) is defined. This horizontal central plane (X, Y) extends midway between the upper edge 12 and the lower edge 14 of the seat backrest. The detection system 15 according to this third embodiment comprises a processor 16, a first pressure sensor 18 arranged on a first zone Z1 located above the first vertical central plane (X, Z), and a second pressure sensor 20 arranged on a second zone Z2 located below the first vertical central plane (X, Z).

Steps 100 to 124 of the detection method according to the present disclosure can be implemented by the detection system according to the second embodiment.

In particular, the detection system according to the second embodiment comprises a step for determining the presence or absence of pressure on a zone. This step comprises the following steps:

i) determining 114 a subsequent characteristic value representative of the capacitive values measured by the pressure sensor considered over a subsequent period, ii) comparing 116 the subsequent characteristic value with the permissible variation range defined for the sensor considered;

iii) determining 118 an absence of pressure on the zone considered if the subsequent characteristic value does not lie within the permissible variation range defined for the sensor considered or determining a presence of pressure if the subsequent characteristic value does lie within the permissible variation range defined for the sensor considered.

The method for detecting an inappropriate posture implemented by the second detection system further comprises a step 122 of repeating steps i) to iii) for a second defined duration D2. The step of generating a warning signal is implemented only if an absence or a presence of pressure is determined continuously for a duration greater than the second defined duration.

When an absence of pressure has been determined in the first zone Z1 and in the second zone Z2, then the warning signal generated is representative of a forward-leaning position of the occupant of the seat.

Preferably, the seat base 4 of the detection system according to a third embodiment comprises two lateral edges 33, 36. A second vertical central plane (X2, Z2) is defined midway between the two lateral edges of the seat base.

The front zone ZA comprises a first front zone ZA1 of the seat base arranged on one side of the second vertical central plane and a second front zone ZA2 of the seat base arranged on the other side of the second vertical central plane (X2, Z2), the rear zone comprises a first rear zone ZR1 of the seat base located on one side of the second vertical central plane (X2, Z2), a second rear zone ZR2 of the seat base located on the other side of the second vertical central plane (X2, Z2).

The detection device 15 comprises a second front pressure sensor 37 arranged on the second front zone ZA2, while the first front pressure sensor 30 is located on the first front zone ZA1.

The detection device 15 further comprises a second rear pressure sensor 37 arranged on the second rear zone ZR2, the first rear pressure sensor 34 being located on the first rear zone ZR1.

The detection method implemented by the detection system according to the third embodiment comprises the following steps:

considering each pressure sensor from the second front pressure sensor 34 and the second rear pressure sensor 37, for each sensor considered:

a) determining 106 a characteristic value representative of the capacitive values measured by the pressure sensor considered over a first period, b) determining 108 a permissible variation range defined for the sensor considered based on the characteristic value, c) determining 114, 116, 118, 120 the presence or absence of pressure on a zone on the basis of the permissible variation range defined for the sensor considered and the capacitive values measured over a subsequent period by the pressure sensor considered arranged in the zone, generating 124 a warning signal when an absence of pressure has been determined on the first front zone AZ1 or on the second front zone ZA2, the warning signal generated being representative of a position of a leg crossed over the other leg of the occupant of the seat.

Alternatively, the detection system according to the fourth embodiment may comprise two pressure sensors as shown in FIG. 6.

Alternatively, the detection system according to another embodiment may comprise four pressure sensors as shown in FIG. 1.

It would be desirable to propose a system for detecting inappropriate posture allowing the occupant of the seat to be informed that he is occupying either an unsafe position with respect to his driving or an uncomfortable position that could eventually lead to fatigue, muscle or back joint pain or neck pain.

The aim of the present disclosure is to propose a reliable and robust method for detecting inappropriate posture.

The object of the present disclosure is a method for detecting an inappropriate posture of an occupant seated on a seat of a vehicle, especially a motor vehicle; the seat having a seat base and a backrest articulated at the seat base, the backrest comprising two lateral edges, an upper edge and a lower edge adjacent to the seat base; a first vertical central plane extending between and midway between the two lateral edges, a first horizontal central plane extending between and midway between the upper edge and the lower edge; the method being implemented by a detection system comprising a processor, at least a first pressure sensor arranged on a first zone located on one side of the first vertical central plane and above the first horizontal central plane, a second pressure sensor arranged on a second zone located on the other side of the first vertical central plane and above the first horizontal central plane, a third pressure sensor arranged on a third zone located on the side of the first vertical central plane and below the first horizontal central plane, a fourth pressure sensor arranged on a fourth zone located on the other side of the first vertical central plane and below the first horizontal central plane; the method comprising a step of activating a measurement phase comprising time periods during which capacitive values are measured by the first, second, third and fourth pressure sensors; the method further comprising the following steps implemented by the processor during the measurement phase:

upon detection of the presence of an occupant on the seat, activating a clock suitable for signaling the end of a first defined duration;

after the first defined duration, considering each pressure sensor from the first, second, third and fourth pressure sensors, for each pressure sensor considered:

a) determining a characteristic value representative of the capacitive values measured by the pressure sensor considered over a first period, b) determining a permissible variation range defined for the sensor considered based on the characteristic value, c) determining the presence or absence of pressure on a zone on the basis of the permissible variation range defined for the sensor considered and the capacitive values measured over a subsequent period by the pressure sensor considered arranged in the zone, generating a warning signal when an absence of pressure has been determined on at least one zone from the zones considered.

The features disclosed in the following paragraphs may optionally be implemented. They can be implemented independently of one another or in combination with one another:

the step of determining the presence or absence of pressure on a zone comprises the following steps:

i) determining a subsequent characteristic value representative of the capacitive values measured by the pressure sensor considered over a subsequent period, ii) comparing the subsequent characteristic value with the permissible variation range defined for the sensor considered;

iii) determining an absence of pressure on the zone considered if the subsequent characteristic value does not lie within the permissible variation range defined for the sensor considered, or determining the presence of pressure if the subsequent characteristic value does lie within the permissible variation range defined for the sensor considered.

The method further comprises a step of repeating steps i) to iii) for a second defined duration and wherein the step of generating a warning signal is implemented only if an absence of pressure is determined continuously for a duration at least equal to the second defined duration.

If a presence of pressure has been determined on the first zone and on the second zone and the absence of pressure has been determined on the third zone and on the fourth zone, then the warning signal generated is representative of a forward pelvis position of the occupant of the seat.

If an absence of pressure has been determined on the first and third zones, and a presence of pressure has been determined on the second zone and the fourth zone, then the warning signal generated is representative of a position of the torso turned to the side.

If an absence of pressure has been determined on the first zone and on the second zone and a presence of pressure has been determined on the third zone and on the fourth zone, then the warning signal generated is representative of a forward-leaning position of the occupant of the seat.

the seat base 4 comprises a front edge and a rear edge, a vertical transverse plane being defined midway between the front edge of the seat base and the rear edge of the seat base, the detection device comprises at least a first front pressure sensor arranged on a front zone of the seat base located in front of the vertical transverse plane, and a first rear pressure sensor arranged on a rear zone of the seat base located behind the vertical transverse plane; the method comprising the following steps:

considering each pressure sensor from the first front pressure sensor and the rear pressure sensor, for each sensor considered:

a) determining a characteristic value representative of the capacitive values measured by the pressure sensor considered over a first period, b) determining a permissible variation range defined for the sensor considered based on the characteristic value, c) determining the presence or absence of pressure on a zone on the basis of the permissible variation range defined for the sensor considered and the capacitive values measured over a subsequent period by the pressure sensor considered arranged in the zone, generating a warning signal when an absence of pressure has been determined on the rear zone, the warning signal generated being representative of a forward pelvis position of the occupant of the seat.

The seat comprises two lateral edges, a second vertical central plane being defined midway between the two lateral edges of the seat base, the front zone comprises a first front zone of the seat base arranged on one side of the second vertical central plane, and a second front zone of the seat base arranged on the other side of the second vertical central plane, the rear zone comprises a first rear zone of the seat base located on one side of the second vertical central plane, and a second rear zone of the seat base located on the other side of the second vertical central plane, the detection device comprises a second front pressure sensor arranged on the second front zone, the first front pressure sensor being located on the first front zone, the detection device further comprises a second rear pressure sensor arranged on the second rear zone, the first rear pressure sensor being located on the first rear zone, the method comprising the following steps:

considering each pressure sensor from the second front pressure sensor (34) and the second rear pressure sensor for each sensor considered:

a) determining a characteristic value representative of the capacitive values measured by the pressure sensor considered over a first period, b) determining a permissible variation range defined for the sensor considered based on the characteristic value, c) determining the presence or absence of pressure on a zone on the basis of the permissible variation range defined for the sensor considered and the capacitive values measured over a subsequent period by the pressure sensor considered arranged in the zone, generating a warning signal when an absence of pressure has been determined on the first front zone or on the second front zone, the warning signal generated being representative of a position of a leg crossed over the other leg of the occupant of the seat.

The present disclosure also relates to at A): a method for detecting an inappropriate posture of an occupant seated on a seat of a vehicle, especially a motor vehicle; the seat having a seat base and a backrest articulated at the seat base, the backrest comprising two lateral edges, a first vertical central plane extending between and midway between the two lateral edges; the method being implemented by a detection system comprising a processor, at least a first pressure sensor arranged on a first zone located on one side of the first vertical central plane, and a second pressure sensor arranged on a second zone located on the other side of the first vertical central plane; the method comprising a step of activating a measurement phase comprising time periods during which capacitive values are measured by the first and the second pressure sensors; the method further comprising the following steps implemented by the processor during the measurement phase:

upon detection of the presence of an occupant on the seat, activating a clock suitable for signaling the end of a first defined duration;

after the first defined duration, considering each pressure sensor from the first pressure sensor and the second pressure sensor, for each sensor considered:

a) determining a characteristic value representative of the capacitive values measured by the pressure sensor considered over a first period, b) determining a permissible variation range defined for the sensor considered based on the characteristic value, c) determining the presence or absence of pressure on a zone on the basis of the permissible variation range defined for the sensor considered and the capacitive values measured during a subsequent period by the pressure sensor considered arranged in the zone, generating a warning signal when an absence of pressure has been determined on at least one zone from the first zone and the second zone (Z2).

The present disclosure also relates to at B): a method for detecting an inappropriate posture of an occupant seated on a seat of a vehicle, especially a motor vehicle; the seat having a seat base and a backrest articulated at the seat base, the backrest comprising an upper edge and a lower edge adjacent to the seat base; a horizontal central plane extending midway between the upper edge and the lower edge; the method being implemented by a detection system comprising a processor, at least a first pressure sensor arranged on a first zone located above the horizontal central plane, and a second pressure sensor arranged on a second zone located below the horizontal central plane; the method comprising a step of activating a measurement phase comprising time periods during which capacitive values are measured by the first and the second pressure sensors; the method further comprising the following steps implemented by the processor during the measurement phase:

upon detection of the presence of an occupant on the seat, activating a clock suitable for signaling the end of a first defined duration;

after the first defined duration, considering each pressure sensor from the first pressure sensor and the second pressure sensor, for each sensor considered:

a) determining a characteristic value representative of the capacitive values measured by the pressure sensor considered over a first period, b) determining a permissible variation range defined for the sensor considered based on the characteristic value, c) determining the presence or absence of pressure on a zone on the basis of the permissible variation range defined for the sensor considered and the capacitive values measured during a subsequent period by the pressure sensor considered arranged in the zone, generating a warning signal when an absence of pressure has been determined on at least one zone from the first zone and the second zone.

According to one embodiment, in the detection method according to (A) and (B), the step of determining the presence or absence of pressure on a zone comprises the following steps:

i) determining a subsequent characteristic value representative of the capacitive values measured by the pressure sensor considered over a subsequent period, ii) comparing the subsequent characteristic value with the permissible variation range defined for the sensor considered;

iii) determining that there is no pressure on the zone considered if the subsequent characteristic value does not lie within the permissible variation range defined for the sensor considered, or determining a presence of pressure when the subsequent characteristic value does lie within the permissible variation range defined for the sensor considered.

According to one embodiment, the detection method according to A) and B) further comprises a step of repeating steps i) to iii) for a second defined duration and wherein the step of generating a warning signal is implemented only if an absence or presence of pressure is determined continuously for a duration greater than the second defined duration.

In the detection method according to A), if an absence of pressure has been determined in the first zone and a presence of pressure has been determined in the second zone, then the warning signal generated is representative of a position of the torso turned to the side.

According to one embodiment, in the detection method according to B), if an absence of pressure has been determined in the first zone and in the second zone, then the warning signal generated is representative of a forward-leaning position of the occupant of the seat.

According to one embodiment, in the detection method according to A) and B), the seat base comprises a front edge and a rear edge, a vertical transverse plane being defined between and midway between the front edge of the seat base and the rear edge of the seat base, the detection device comprises at least a first front pressure sensor arranged on a front zone of the seat base located in front of the vertical transverse plane, and a first rear pressure sensor arranged on a rear zone of the seat base located behind the vertical transverse plane, the method comprising the following steps:

considering each pressure sensor from the first front pressure sensor and the first rear pressure sensor, for each sensor considered:

a) determining a characteristic value representative of the capacitive values measured by the pressure sensor considered over a first period, b) determining a permissible variation range defined for the sensor considered based on the characteristic value, c) determining the presence or absence of pressure on a zone on the basis of the permissible variation range defined for the sensor considered and the capacitive values measured during a subsequent period by the pressure sensor considered arranged in the zone, generating a warning signal when an absence of pressure has been determined on the rear zone, the warning signal generated being representative of a forward pelvis position of the occupant of the seat.

According to one embodiment, in the detection method according to A) and B), the seat base comprises two lateral edges, a second vertical central plane being defined midway between the two lateral edges of the seat base, the front zone comprises a first front zone of the seat base arranged on one side of the second vertical central plane and a second front zone of the seat base arranged on the other side of the second vertical central plane, the rear zone comprises a first rear zone of the seat base located on one side of the second vertical central plane, and a second rear zone of the seat base located on the other side of the second vertical central plane, the detection device comprises a second front pressure sensor arranged on the second front zone, the first front pressure sensor being located on the first front zone, the detection device further comprises a second rear pressure sensor arranged on the second rear zone, the first rear pressure sensor being located on the first rear zone, the method comprising the following steps:

considering each pressure sensor from the second front pressure sensor and the second rear pressure sensor, for each sensor considered:

a) determining a characteristic value representative of the capacitive values measured by the pressure sensor considered over a first period, b) determining a permissible variation range defined for the sensor considered based on the characteristic value, c) determining the presence or absence of pressure on a zone on the basis of the permissible variation range defined for the sensor considered and the capacitive values measured over a subsequent period by the pressure sensor considered arranged in the zone, generating a warning signal when an absence of pressure has been determined on the first front zone or on the second front zone, the warning signal generated being representative of a position of a leg crossed over the other leg of the occupant of the seat.

The present disclosure relates to a method for detecting an inappropriate posture of an occupant seated on a seat of a vehicle, the method comprising the following steps:

after a first defined duration following detection of the presence of an occupant on the seat, for each pressure sensor of the detection system:

a) determining (106) a characteristic value representative of the capacitive values measured by the pressure sensor considered over a first period, b) determining (108) a permissible variation range defined for the sensor considered based on the characteristic value, c) determining (114, 116, 118, 120, 122) the absence of pressure on a zone on the basis of the permissible variation range defined for the sensor considered and the capacitive values measured over a subsequent period, generating (124) a warning signal when an absence of pressure has been determined on at least one zone.

The invention claimed is:

1. A method for detecting an inappropriate posture of an occupant seated on a seat of a vehicle; the seat having a seat base and a backrest articulated at the seat base, the backrest comprising two lateral edges, an upper edge and a lower edge adjacent to the seat base; a first vertical central plane extending between and midway between the two lateral edges, a first horizontal central plane extending between and midway between the upper edge and the lower edge; the method being implemented by a detection system comprising a processor, at least a first pressure sensor arranged on a first zone located on one side of the first vertical central plane and above the first horizontal central plane, a second pressure sensor arranged on a second zone located on the other side of the first vertical central plane and above the first horizontal central plane, a third pressure sensor arranged on a third zone located on the one side of the first vertical central plane and below the first horizontal central plane, a fourth pressure sensor arranged on a fourth zone located on the other side of the first vertical central plane and below the first horizontal central plane; the method comprising a step of activating a measurement phase comprising time periods during which capacitive values are measured by the first, second, third and fourth pressure sensors; the method further comprising the following steps implemented by the processor during the measurement phase:

upon detection of the presence of an occupant on the seat, activating a clock suitable for signaling the end of a first defined duration;

after the first defined duration, considering each pressure sensor from the first, second, third and fourth pressure sensors, for each pressure sensor considered:

a) determining a characteristic value representative of the capacitive values measured by the pressure sensor considered over a first period, b) determining a permissible variation range defined for the pressure sensor considered based on the characteristic value, c) determining the presence or absence of pressure on a zone on the basis of the permissible variation range defined for the pressure sensor considered and the capacitive values measured over a subsequent period by the pressure sensor considered arranged in the zone, generating a warning signal when an absence of pressure has been determined on at least one zone from the zones considered, wherein the step of determining the presence or absence of pressure on a zone comprises the following steps:

i) determining a subsequent characteristic value representative of the capacitive values measured by the pressure sensor considered over a subsequent period, ii) comparing the subsequent characteristic value with the permissible variation range defined for the pressure sensor considered;

iii) determining an absence of pressure on the zone considered if the subsequent characteristic value does not lie within the permissible variation range defined for the pressure sensor considered or determining a presence of pressure when the subsequent characteristic value does lie within the permissible variation range defined for the pressure sensor considered.

2. The method of claim 1, which further comprises a step of repeating steps i) to iii) for a second defined duration and wherein the step of generating a warning signal is only implemented if an absence of pressure is determined continuously for a duration at least equal to the second defined duration.

3. The method of claim 1, wherein if a presence of pressure has been determined on the first zone and on the second zone and an absence of pressure has been determined on the third zone and on the fourth zone, then the warning signal generated is representative of a forward pelvis position of the occupant of the seat.

4. The method of claim 1, wherein if an absence of pressure has been determined on the first zone and the third zone, and a presence of pressure has been determined on the second zone and the fourth zone, then the warning signal generated is representative of a position of the torso turned to the side.

5. The method of claim 1, wherein if an absence of pressure has been determined on the first zone and on the second zone and a presence of pressure has been determined on the third zone and on the fourth zone then the warning signal generated is representative of a forward-leaning position of the occupant of the seat.

6. The method of claim 1, wherein the seat base comprises a front edge and a rear edge, a vertical transverse plane being defined midway between the front edge of the seat base and the rear edge of the seat base, the detection system comprises at least a first front pressure sensor arranged on a front zone of the seat base located in front of the vertical transverse plane, and a first rear pressure sensor arranged on a rear zone of the seat base located behind the vertical transverse plane; the method comprising the following steps:

considering each pressure sensor from the first front pressure sensor and the first rear pressure sensor, for each pressure sensor considered:

a) determining a characteristic value representative of the capacitive values measured over the first period by the pressure sensor considered among the first front pressure sensor and the first rear pressure sensor, b) determining a permissible variation range defined for the sensor considered based on the characteristic value, c) determining the presence or absence of pressure on a zone on the basis of the permissible variation range defined for the sensor considered and the capacitive values measured over a subsequent period by the pressure sensor considered arranged in the zone, generating a warning signal when an absence of pressure has been determined on the rear zone, the warning signal generated being representative of a forward pelvis position of the occupant of the seat.

7. The method of claim 6, wherein the seat base comprises two lateral edges, a second vertical central plane being defined midway between the two lateral edges of the seat base, the front zone comprises a first front zone of the seat base arranged on one side of the second vertical central plane, and a second front zone of the seat base arranged on the other side of the second vertical central plane, the rear zone comprises a first rear zone of the seat base located on one side of the second vertical central plane, and a second rear zone of the seat base located on the other side of the second vertical central plane, the detection system comprises a second front pressure sensor arranged on the second front zone, the first front pressure sensor being located on the first front zone, the detection system further comprises a second rear pressure sensor arranged on the second rear zone, the first rear pressure sensor being located on the first rear zone, the method comprising the following steps:

considering each pressure sensor from the second front pressure sensor and the second rear pressure sensor for each sensor considered:

a) determining a characteristic value representative of the capacitive values measured over the first period by the pressure sensor considered among the second front pressure sensor and the second rear pressure sensor, b) determining a permissible variation range defined for the sensor considered based on the characteristic value, c) determining the presence or absence of pressure on a zone on the basis of the permissible variation range defined for the sensor considered and the capacitive values measured over a subsequent period by the pressure sensor considered arranged in the zone, generating a warning signal when an absence of pressure has been determined on the first front zone or on the second front zone, the warning signal generated being representative of a position of a leg crossed over the other leg of the occupant of the seat.

8. A method for detecting an inappropriate posture of an occupant seated on a seat of a vehicle; the seat having a seat base and a backrest articulated at the seat base, the backrest comprising two lateral edges, a first vertical central plane extending between and midway between the two lateral edges; the method being implemented by a detection system comprising a processor, at least a first pressure sensor arranged on a first zone located on one side of the first vertical central plane, and a second pressure sensor arranged on a second zone located on the other side of the first vertical central plane; the method comprising a step of activating a measurement phase comprising time periods during which capacitive values are measured by the first and the second pressure sensors; the method further comprising the following steps implemented by the processor during the measurement phase:

upon detection of the presence of an occupant on the seat, activating a clock suitable for signaling the end of a first defined duration;

after the first defined duration, considering each pressure sensor from the first pressure sensor and the second pressure sensor, for each pressure sensor considered:

a) determining a characteristic value representative of the capacitive values measured by the pressure sensor considered over a first period, b) determining a permissible variation range defined for the pressure sensor considered based on the characteristic value, c) determining the presence or absence of pressure on a zone on the basis of the permissible variation range defined for the pressure sensor considered and the capacitive values measured over a subsequent period by the pressure sensor considered arranged in the zone, generating a warning signal when an absence of pressure has been determined on at least one zone from the first zone and the second zone, wherein the step of determining the presence or absence of pressure on a zone comprises the following steps:

i) determining a subsequent characteristic value representative of the capacitive values measured by the pressure sensor considered over a subsequent period, ii) comparing the subsequent characteristic value with the permissible variation range defined for the pressure sensor considered;

iii) determining an absence of pressure on the zone considered if the subsequent characteristic value does not lie within the permissible variation range defined for the pressure sensor considered or determining a presence of pressure when the subsequent characteristic value does lie within the permissible variation range defined for the pressure sensor considered.

9. The method of claim 8, wherein the seat base comprises a front edge and a rear edge, a vertical transverse plane being defined between and midway between the front edge of the seat base and the rear edge of the seat base, the detection system comprises at least a first front pressure sensor arranged on a front zone of the seat base located in front of the vertical transverse plane, and a first rear pressure sensor arranged on a rear zone of the seat base located behind the vertical transverse plane, the method comprising the following steps:

considering each pressure sensor from the first front pressure sensor and the first rear pressure sensor, for each sensor considered:

a) determining a characteristic value representative of the capacitive values measured over the first period by the pressure sensor considered among the first front pressure sensor and the first rear pressure sensor, b) determining a permissible variation range defined for the sensor considered based on the characteristic value, c) determining the presence or absence of pressure on a zone on the basis of the permissible variation range defined for the sensor considered and the capacitive values measured over a subsequent period by the pressure sensor considered arranged in the zone, generating a warning signal when an absence of pressure has been determined on the rear zone, the warning signal generated being representative of a forward pelvis position of the occupant of the seat.

10. A method for detecting an inappropriate posture of an occupant seated on a seat of a vehicle; the seat having a seat base and a backrest articulated at the seat base, the backrest comprising an upper edge and a lower edge adjacent to the seat base; a horizontal central plane extending midway between the upper edge and the lower edge; the method being implemented by a detection system comprising a processor, at least a first pressure sensor arranged on a first zone located above the horizontal central plane, and a second pressure sensor arranged on a second zone located below the horizontal central plane; the method comprising a step of activating a measurement phase comprising time periods during which capacitive values are measured by the first and the second pressure sensors; the method further comprising the following steps implemented by the processor during the measurement phase:

upon detection of the presence of an occupant on the seat, activating a clock suitable for signaling the end of a first defined duration;

after the first defined duration, considering each pressure sensor from the first pressure sensor and the second pressure sensor, for each sensor considered:

a) determining a characteristic value representative of the capacitive values measured by the pressure sensor considered over a first period, b) determining a permissible variation range defined for the sensor considered based on the characteristic value, c) determining the presence or absence of pressure on a zone on the basis of the permissible variation range defined for the sensor considered and the capacitive values measured over a subsequent period by the pressure sensor considered arranged in the zone, generating a warning signal when an absence of pressure has been determined on at least one zone from the first zone and the second zone, wherein the step of determining the presence or absence of pressure on a zone comprises the following steps:

i) determining a subsequent characteristic value representative of the capacitive values measured by the pressure sensor considered over a subsequent period, ii) comparing the subsequent characteristic value with the permissible variation range defined for the pressure sensor considered;

iii) determining an absence of pressure on the zone considered if the subsequent characteristic value does not lie within the permissible variation range defined for the pressure sensor considered or determining a presence of pressure when the subsequent characteristic value does lie within the permissible variation range defined for the pressure sensor considered.

* * * * *